(12) United States Patent
Honda

(10) Patent No.: US 10,743,928 B2
(45) Date of Patent: Aug. 18, 2020

(54) ENERGY TREATMENT DEVICE

(71) Applicant: OLYMPUS CORPORATION, Hachioji-shi, Tokyo (JP)

(72) Inventor: Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 273 days.

(21) Appl. No.: 15/837,461

(22) Filed: Dec. 11, 2017

(65) Prior Publication Data

US 2018/0099161 A1 Apr. 12, 2018

Related U.S. Application Data

(63) Continuation of application No. PCT/JP2016/063888, filed on May 10, 2016.

(30) Foreign Application Priority Data

Jun. 17, 2015 (JP) .................................. 2015-121627

(51) Int. Cl.
*A61B 18/12* (2006.01)
*A61B 18/08* (2006.01)
(Continued)

(52) U.S. Cl.
CPC .... *A61B 18/085* (2013.01); *A61B 17/320092* (2013.01); *H01L 35/32* (2013.01);
(Continued)

(58) Field of Classification Search
CPC .......... A61B 17/320092; A61B 18/085; A61B 2017/00411; A61B 2017/00415;
(Continued)

(56) References Cited

U.S. PATENT DOCUMENTS 6,113,598 A * 9/2000 Baker ................ A61B 18/1445
606/38
6,500,176 B1 * 12/2002 Truckai .............. A61B 18/1445
606/205
(Continued)

FOREIGN PATENT DOCUMENTS

JP 2005-514102 A 5/2005
JP 2007-509652 A 4/2007
(Continued)

OTHER PUBLICATIONS

Dec. 19, 2017 International Preliminary Report on Patentability issued in International Patent Application No. PCT/JP2016/063888.
(Continued)

*Primary Examiner* — Michael F Peffley
(74) *Attorney, Agent, or Firm* — Oliff PLC

(57) ABSTRACT

An energy treatment device includes a treatment portion that receives a supply of energy and treats a treatment target, a controller that controls the supply of energy with respect to the treatment portion, a converter that is configured to receive heat energy generated with the treatment of the treatment target, and to convert a temperature difference into an electric energy, and a receiver that receives the electric energy converted at the converter.

4 Claims, 3 Drawing Sheets

(51) Int. Cl.
*A61B 17/32* (2006.01)
*H01L 35/32* (2006.01)
*H02J 7/00* (2006.01)
*A61B 17/00* (2006.01)
*A61B 18/00* (2006.01)

(52) U.S. Cl.
CPC ... *H02J 7/0013* (2013.01); *A61B 2017/00411* (2013.01); *A61B 2017/00415* (2013.01); *A61B 2017/00734* (2013.01); *A61B 2017/320094* (2017.08); *A61B 2017/320095* (2017.08); *A61B 2018/00577* (2013.01); *A61B 2018/00601* (2013.01); *A61B 2018/00994* (2013.01); *A61B 2018/1226* (2013.01)

(58) Field of Classification Search
CPC ......... A61B 2017/00734; A61B 2017/320094; A61B 2017/320095; A61B 2018/00601; A61B 2018/00994; A61B 2018/1226; A61B 2018/00577; H01L 35/32; H02J 7/0013
See application file for complete search history.

(56) References Cited

U.S. PATENT DOCUMENTS

| | | | |
|---|---|---|---|
| 2003/0125734 A1 | 7/2003 | Mollenauer | |
| 2004/0093041 A1 | 5/2004 | MacDonald | |
| 2013/0345695 A1* | 12/2013 | McPherson | A61B 18/1477 606/34 |
| 2015/0190189 A1* | 7/2015 | Yates | A61B 18/1206 606/28 |

FOREIGN PATENT DOCUMENTS

| | | |
|---|---|---|
| JP | 2011-176970 A | 9/2011 |
| JP | 2013-250019 A | 12/2013 |
| JP | 2014-146708 A | 8/2014 |

OTHER PUBLICATIONS

Apr. 18, 2017 Office Action issued in Japanese Patent Application No. 2017-501429.

Jul. 19, 2016 International Search Report issued in International Patent Application No. PCT/JP2016/063888.

* cited by examiner

10,743,928 B2

ENERGY TREATMENT DEVICE

CROSS-REFERENCE TO RELATED APPLICATIONS

This application is a Continuation Application of PCT Application No. PCT/JP2016/063888, filed May 10, 2016 and based upon and claims the benefit of priority from prior Japanese Patent Application No. 2015-121627, filed Jun. 17, 2015, the entire contents of which are incorporated herein by reference.

BACKGROUND OF THE INVENTION

1. Field of the Invention

The present invention relates generally to an energy treatment device that performs treatment on biotissue.

2. Description of the Related Art

Jpn. Pat. Appln. KOKAI Publication No. 2014-146708 (Patent Literature 1) discloses a thermoelectric power generation module that is attached to a human skin surface, and generates electric power using a human body as a heat source. The thermoelectric power generation module comprises a thermoelectric power generation unit and a secondary battery.

In an energy treatment device used in a state where it is separated from a box-like power source device (a cordless state), extending a battery's endurance time is an important factor for improving convenience for an operator.

BRIEF SUMMARY OF THE INVENTION

An energy treatment device of a certain aspect of the present invention comprises a treatment portion that receives a supply of energy and treats a treatment target, a controller that controls the supply of energy to the treatment portion, a converter that is configured to receive heat energy generated along with the treatment of the treatment target, and converts a temperature difference into an electric energy, and a receiver that receives the electric energy converted by the converter.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

[First Embodiment]

A first embodiment of an energy treatment device of the present invention will be explained with reference to FIGS. 1 to 4. An energy treatment device 11 (a hand piece) of the following embodiment is, for example, suitably used in a state of being physically separated from a power source device (a power source box) connected to a power source of a building, that is, in a cordless state. However, it is also possible to be used in a state of being connected to the power source device via a cable. Here, the energy treatment device 11 will be explained by referring to one of the two directions in parallel with a central axis C of a housing main body 21 as a distal end direction C1, and the opposite of the distal end direction as a proximal end direction C2.

Figure 1:
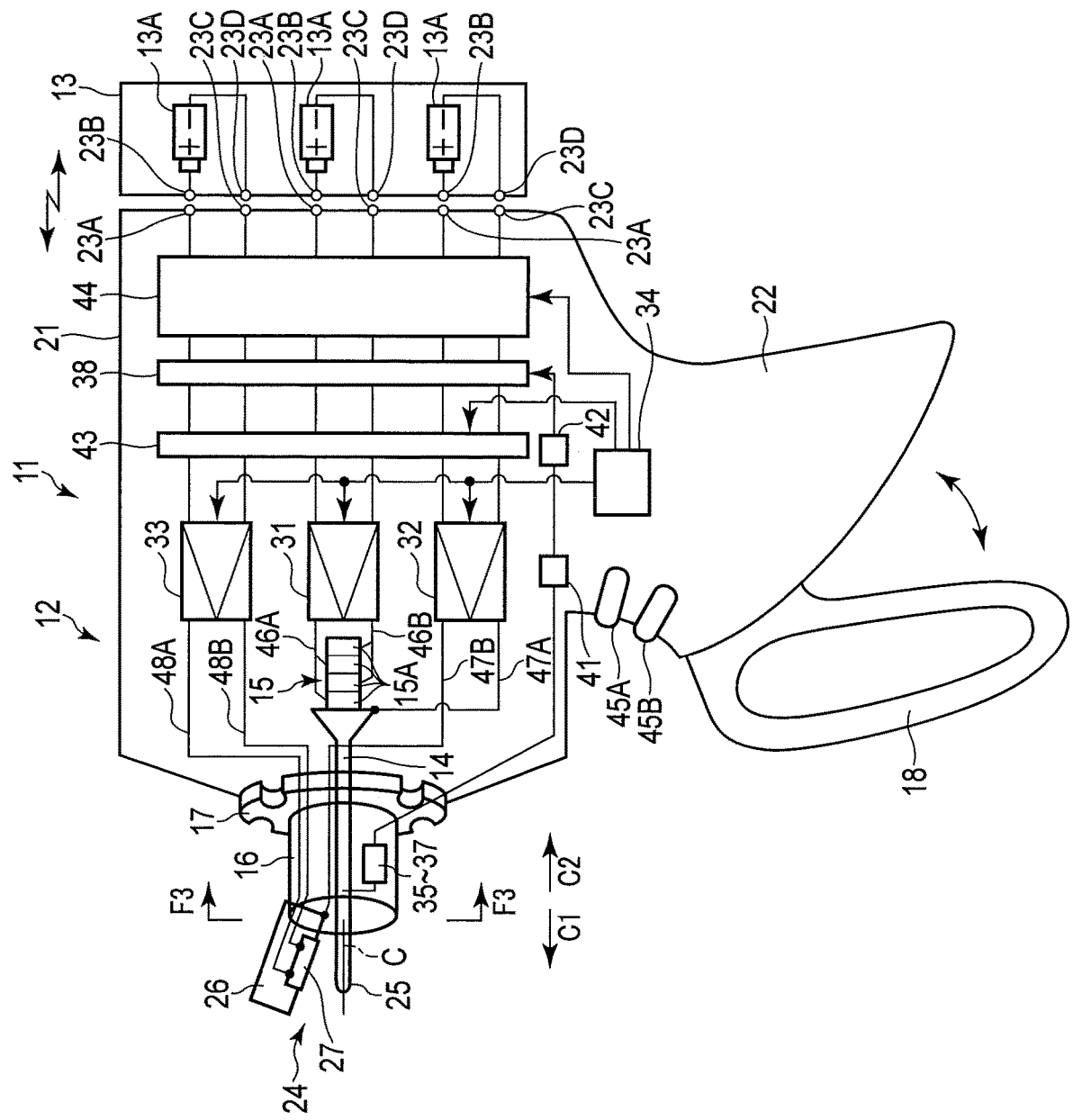
FIG. 1 is a schematic diagram showing an energy treatment device according to a first embodiment.

As shown in FIG. 1, the energy treatment device 11 comprises a housing 12 which can be held by hand by an operator, a battery unit 13 (a battery) detachably attached to the housing 12, a rod-like vibration transmitting portion 14, a part of which is accommodated in the housing 12 and a distal side part of which protrudes outside the housing 12, an ultrasonic transducer 15 fixed on a proximal side of the vibration transmitting portion 14, a cylindrical sheath 16 revolvably attached with respect to the housing 12 and covering the vibration transmitting portion 14, a revolving knob 17 fixed on the sheath 16, and a handle 18 (a movable handle) rotatably provided with respect to the housing 12.

The housing 12 comprises a housing main body 21 and a grip 22 (fixed handle) extending from the housing main body 21 towards a direction intersecting the central axis C of the housing main body 21. The battery unit 13 comprises a plurality of (for example, three) batteries 13A. However, the batteries are not limited to this number, and may also be one. By attaching the battery unit 13 to the housing 12, an electric contact point 23A comes in contact with an electric contact point 23B, and an electric contact point 23C comes in contact with an electric contact point 23D. This allows the battery unit 13 to be electrically connected to a charge circuit 44 side mentioned later on.

The vibration transmitting portion 14 is formed of a conductive metal material. The ultrasonic transducer 15 includes a plurality of piezoelectric elements 15A that convert an electric energy (alternating-current power) into ultrasonic vibration. The sheath 16 is cylindrically formed by a conductive metal material. In FIG. 1, the length of the sheath 16 is shortened and shown; however, the length is actually several to several tens of times longer than the length shown in the drawing. The revolving knob 17 is revolvable about the central axis C with respect to the housing 12. By revolving the revolving knob 17, the sheath 16, the vibration transmitting portion 14 (a first gripping piece 25), the ultrasonic transducer 15, and a second gripping piece 26 can be revolved about the central axis C with respect to the housing 12.

Figure 2:
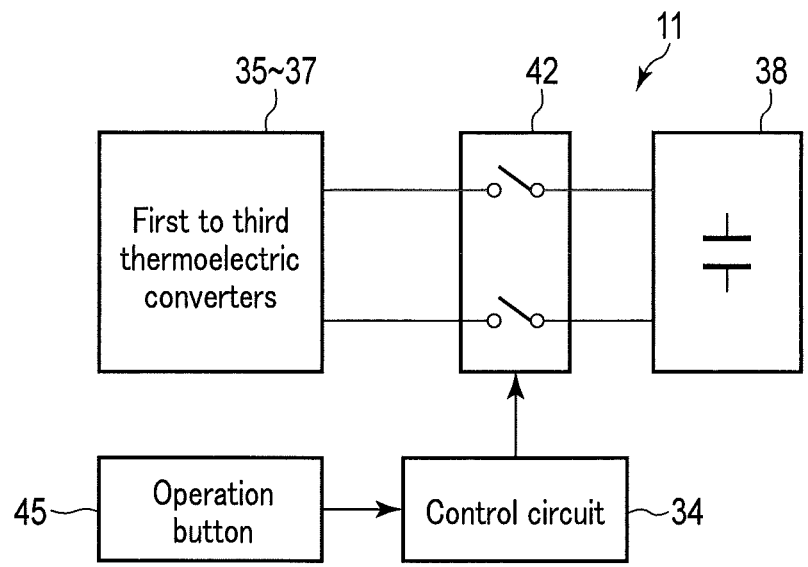
FIG. 2 is a block diagram showing configurations of a control circuit, first to third thermoelectric converters, a first switch portion, and a tank of the energy treatment device shown in FIG. 1.

As shown in FIG. 1 and FIG. 2, the energy treatment device 11 comprises a treatment portion 24 (an end effector) provided on the distal end direction C1 side (the distal end direction C1 side of the sheath 16) of the vibration transmitting portion 14, a heater 27 provided on the second gripping piece 26 of the treatment portion 24 explained later on, first to third amplifier circuits 31 to 33 capable of amplifying electric current for providing various energies to the treatment portion 24, a control circuit 34 that controls the first to third amplifier circuits 31 to 33, first to third thermoelectric converters 35 to 37 (converters) that convert heat energy stored in the treatment portion 24 into electric energy, a tank 38 for temporary accumulating the electric energy generated at the first to third thermoelectric converters 35 to 37, an electric power converter 41 interposed between the first to third thermoelectric converters 35 to 37 and the tank 38, a first switch portion 42 capable of connecting and disconnecting an electrical connection between the first to third thermoelectric converters 35 to 37 and the tank 38, a second switch portion 43 capable of connecting and disconnecting an electrical connection between the tank 38 and the first to third amplifier circuits 31 to 35, a charge circuit 44 that charges the battery unit 13 with the electric energy stored in the tank 38, and a plurality of operation buttons 45 for an operator to switch an output of each of the various energies on/off with respect to the treatment portion 24.

Figure 3:
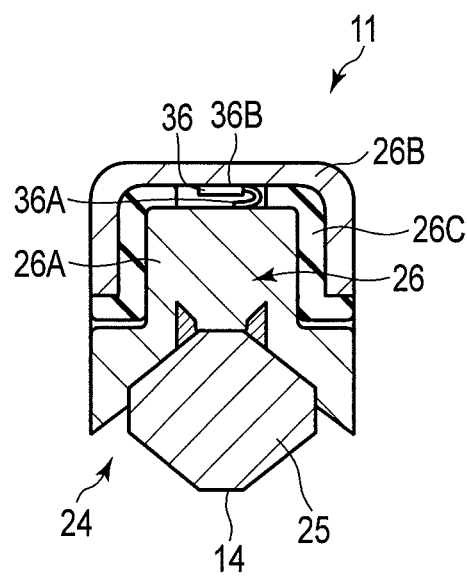
FIG. 3 is a cross-sectional view taken along line F3-F3 of the energy treatment device shown in FIG. 1.

The treatment portion 24 is capable of treating the treatment target by receiving energy supplied from the ultrasonic transducer 15, the second amplifier circuit 32, and the heater 27. The treatment portion 24 comprises the first gripping piece 25 provided on the distal end direction C1 side of the vibration transmitting portion 14, and the second gripping piece 26 (jaw) rotatably attached to the distal end portion of the sheath 16. When treating the treatment target by ultrasonic vibration caused by an ultrasonic energy, the temperature of the first gripping piece 25 becomes as high as, for example, 200 to 300 degrees. As shown in FIG. 3, the second gripping piece 26 comprises a second gripping piece main body 26A formed by a conductive metal material, a metal cover 26B that covers the second gripping piece main body 26A, and an insulating member 26C interposed between the second gripping piece main body 26A and the cover 26B.

By rotating the second gripping piece 26, the first gripping piece 25 and the second gripping piece 26 can be open or closed with respect to each other. In other words, the first gripping piece 25 and the second gripping piece 26 of the treatment portion 24 configure a pair of clamping members that is capable of clamping and holding a biotissue of the treatment target. By rotating the handle 18 with respect to the housing 12, the operator is capable of performing an open/close operation of this second gripping piece 26. In other words, the handle 18 is rotated to move a cylindrical movable pipe provided on the inner side of the sheath 16 along the central axis C of the sheath 16, thereby causing the second gripping piece 26 to perform an open/close motion. In the present embodiment, the end effector that uses a supplied treatment energy to treat a treatment target of a biotissue, etc. is configured by the first gripping piece 25 and the second gripping piece 26. Upon treatment, the treatment target is gripped between the first gripping piece 25 and the second gripping piece 26, and the treatment energy is applied thereto.

The heater 27 is capable of converting an electric energy (direct-current power) into a heat energy. As shown in FIG. 1, the first amplifier circuit 31 for ultrasonic energy is electrically connected to the ultrasonic transducer 15 via electric passages 46A and 46B, and is capable of supplying a suitably amplified electric current to the ultrasonic transducer 15. The second amplifier circuit 32 for high-frequency energy is electrically connected to the vibration transmitting portion 14 via an electric passage 47A, and is electrically connected to the second gripping piece 26 via an electric passage 47B. The second amplifier circuit 32 is capable of supplying a suitably amplified electric current (a high-frequency current) to the vibration transmitting portion 14 and the second gripping piece 26. The third amplifier circuit 33 for heat energy is electrically connected to the heater 27 via electric passages 48A and 48B, and is capable of supplying a suitably amplified electric current to the heater 27.

The control circuit 34 (a controller) comprises a CPU, a ROM, and a RAM, etc., and a motherboard (a substrate) that mounts them and has wirings formed thereon to connect each other. The control circuit 34 is capable of controlling the first to third amplifier circuits 31 to 33 to control the supply of energy used for treatment at the treatment portion 24.

Figure 4:
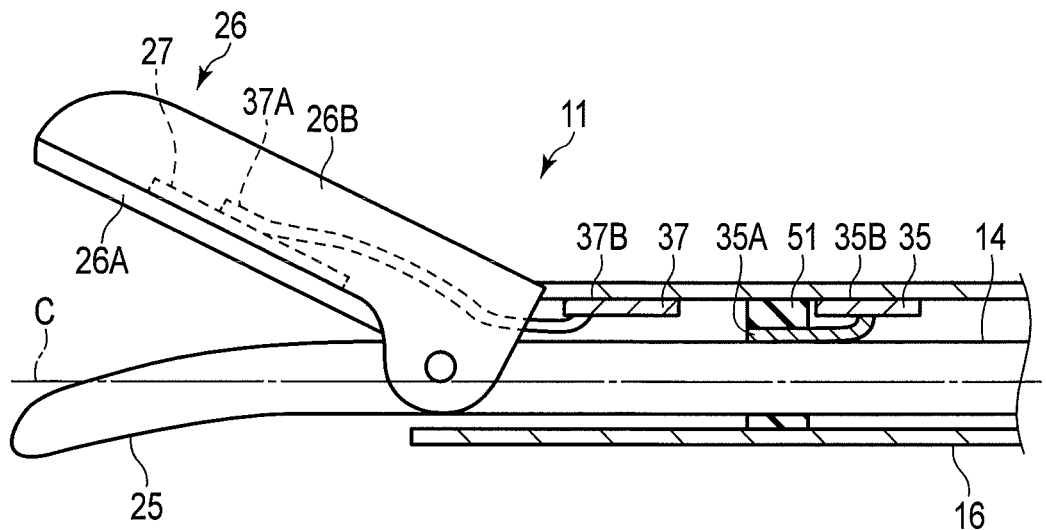
FIG. 4 is a cross-sectional view obtained by cutting a sheath periphery structure of the energy treatment device shown in FIG. 1 by a surface including a central axis.

As shown in FIG. 4, the first thermoelectric converter 35 is provided on, for example, the inner surface of the sheath 16. The first thermoelectric converter 35 is provided corresponding to a heat energy originated from the ultrasonic energy. The first thermoelectric converter 35 is configured by a so-called thermocouple, and comprises a first hot contact point 35A and a first cold contact point 35B. The first hot contact point 35A is fixed to a node position of the ultrasonic vibration of the vibration transmitting portion 14. The first hot contact point 35A is held in a state where it is in contact with the vibration transmitting portion 14 by a ring member 51 with elastic resiliency that holds the vibration transmitting portion 14 at a center portion of the sheath 16. The first cold contact point 35B is fixed to a place where the temperature is lower than the treatment portion 24, such as on the inner surface of the sheath 16.

The second thermoelectric converter 36 is provided on, for example, the inner surface of the cover 26B of the second gripping piece 26. The second thermoelectric converter 36 is provided corresponding to the heat energy originated from the high-frequency energy. The second thermoelectric converter 36 is configured by a so-called thermocouple, and comprises a second hot contact point 36A and a second cold contact point 36B. The second hot contact point 36A is fixed to the second gripping piece main body 26A. The second cold contact point 36B is fixed to a place where the temperature is lower than the treatment portion 24, such as on the inner surface of the cover 26B.

The third thermoelectric converter 37 is provided on, for example, the inner surface of the sheath 16. The third thermoelectric converter 37 is provided corresponding to the heat energy originated from the heater 27. The third thermoelectric converter 37 is configured by a so-called thermocouple, and comprises a third hot contact point 37A and a third cold contact point 37B. The third hot contact point 37A is fixed on a surface of the heater 27. In the present embodiment, the third hot contact point 37A is fixed on a back surface of a plate-like heater 27; however, the fixed position of the third hot contact point 37A is not limited to this, and may be on the front surface of the heater 27, or on a heat transfer portion where heat of the heater 27 is transferred. The third cold contact point 37B is fixed to a place where the temperature is lower than the treatment portion 24, such as on the inner surface of the sheath 16. The first to third thermoelectric converters 35 to 37 are examples of converters that convert the temperature difference into electric energy.

The tank 38 is, for example, configured by a capacitor. The electric power converter 41 is interposed between the first to third thermoelectric converters 35 to 37 and the tank 38. The electric power converter 41 is, for example, configured by a DC-DC converter, etc. and is capable of converting the voltage generated at the first to third thermoelectric converters 35 to 37 into a voltage suitable for being accumulated in the tank 38. In the present embodiment, the tank 38, the charge circuit 44, and the battery unit 13 are examples of receivers that receive the electric energy converted at the converters.

The first switch portion 42 and the second switch portion 43 are configured by a general relay circuit. The first switch portion 42 and the second switch portion 43 are preferably configured by, for example, a semiconductor relay (a photo MOS relay, a photocoupler, an FET, a transistor gate); however, may also be configured by a mechanical relay circuit. Under the control of the control circuit 34, the first switch portion 42 is capable of switching between a connected state in which the first to third thermoelectric converters 35 to 37 and the tank 38 are electrically connected, and a disconnected state in which the first to third thermoelectric converters 35 to 37 and the tank 38 are electrically disconnected. Under the control of the control circuit 34, the second switch portion 43 is capable of switching between a connected state in which the tank 38 (the battery unit 13) and the first to third amplifier circuits 31 to 33 are electrically connected, and a disconnected state in which the tank 38 (the battery unit 13) and the first to third amplifier circuits 31 to 33 are electrically disconnected.

The charge circuit 44 is interposed between the tank 38 and the battery unit 13. Under the control of the control circuit 34, the charge circuit 44 is capable of charging the battery unit 13 from the tank 38. When the amplified electric current is output from the first to third amplifier circuits 31 to 33 (when treatment is performed by the treatment portion 24), the charge circuit 44 does not charge the battery unit 13 from the tank 38. When the output of the electric current from the first to third amplifier circuits 31 to 33 is stopped (when treatment is not performed by the treatment portion 24), the charge circuit 44 charges the battery unit 13 from the tank 38.

An operation button 45A corresponds to an incision mode for incising or ablating a biotissue. An operation button 45B corresponds to a solidification mode for solidifying the biotissue. When the operator operates the operation button 45A or 45B, the control circuit 34 controls the first to third amplifier circuits 31 to 33 to allow an energy suitable for each mode to be provided to the treatment portion 24. In such case, the control circuit 34 controls the first amplifier circuit 31, for the first amplifier circuit 31 to convert the electric energy (direct-current power) supplied from the battery unit 13 into an electric energy (alternating-current power) that generates ultrasonic vibration. The electric energy supplied from the first amplifier circuit 31 is supplied to the ultrasonic transducer 15, at which ultrasonic vibration is generated. The ultrasonic vibration is transmitted to the treatment portion 24 (the first gripping piece 25) through the vibration transmitting portion 14 as a treatment energy. In the above manner, the ultrasonic energy is applied to the treatment target at the treatment portion 24.

The control circuit 34 controls the second amplifier circuit 32, for the second amplifier circuit 32 to convert the electric energy (direct-current power) supplied from the battery unit 13 into a high-frequency electric energy (alternating-current power). The high-frequency electric energy supplied from the second amplifier circuit 32 is supplied to the first gripping piece 25 of the treatment portion 24 via the electric passage 47A, as well as to the second gripping piece 26 of the treatment portion 24 via an electric passage 47B. The high-frequency electric energy supplied to the first gripping piece 25 and the second gripping piece 26 as a treatment energy allows the first gripping piece 25 and the second gripping piece 26 to function as electrodes (bipolar electrodes) having potentials different from each other. In the above manner, a treatment (a bipolar treatment) for applying the high-frequency electric current (the high-frequency energy) to the treatment target is performed between the first gripping piece 25 and the second gripping piece 26.

Furthermore, the control circuit 34 controls the third amplifier circuit 33 so that the third amplifier circuit 33 converts the electric energy (direct-current power) supplied from the battery unit 13 into an electric energy (direct-current power) that generates heat. The electric energy supplied from the third amplifier circuit 33 is supplied to the heater 27 via the electric passages 48A and 48B to generate heat (treatment energy) at the heater 27. In the above manner, the heat energy is applied to the treatment target at the treatment portion 24.

In the present embodiment, as the treatment energy supplied to the treatment portion 24, ultrasonic vibration, a high-frequency electric energy, and heat can be generated; however, one or two items among the ultrasonic vibration, the high-frequency electric energy, and the heat may also be generated as the treatment energy. Furthermore, an energy different from the ultrasonic vibration, the high-frequency electric energy, and the heat may also be supplied to the treatment portion 24 as the treatment energy.

In the following, with reference to FIG. 1 to FIG. 4, an operation of the energy treatment device 11 of the present embodiment will be explained. The operator is capable of using the energy treatment device 11 to perform treatment on a treatment target region. That is, in a state where the housing 12 is gripped by the operator, when the operator clutches the treatment target with the treatment portion 24 by operating the handle 18 and operates the operation button 45A in such state, an energy in a mode suitable for incising the biotissue is provided to the treatment portion 24. When the operation button 45B is operated, an energy in a mode suitable for coagulating the biotissue is provided to the treatment portion 24.

Specifically, the electric power supplied from the battery unit 13 is supplied to the first to third amplifier circuits 31 to 33 via the second switch portion 43 under the control of the control circuit 34, is converted into a suitable electric energy at each of the first to third amplifier circuits 31 to 33, and is output from the treatment portion 24 as the ultrasonic energy, the high-frequency energy, and the heat energy. In the case where the electric energy is accumulated in the tank 38, the electric energy may be supplied to the first to third amplifier circuits 31 to 33, and converted into a suitable electric energy at each of the first to third amplifier circuits 31 to 33, to output various kinds of energies from the treatment portion 24. In the used state, where various kinds of energies are output from the treatment portion 24, the second switch portion 43 is in a connected state in which the battery unit 13 and the first to third amplifier circuits 31 to 33 are electrically connected. However, in the used state, the first switch portion 42 is in a disconnected state in which the first to third thermoelectric converters 35 to 37 and the tank 38 are electrically disconnected.

In the case where the operator has completed the treatment, or has temporarily stopped the treatment, and the operation button 45 depressed by the operator has been released (has become an unused state), the supply of energy to the treatment portion 24 will be stopped. The control circuit 34 controls the first switch portion 42 so as to bring the first to third thermoelectric converters 35 to 37 and the tank 38 to a connected state in which they are electrically connected from the above disconnected state. The first switch portion 42 may be switched from the disconnected state to the connected state immediately after releasing the depressed operation button 45, or after a predetermined time (several seconds to several tens of seconds) from releasing the depressed operation button 45.

In this state, at the first thermoelectric converter 35, the temperature difference between the first hot contact point 35A (the first gripping piece 25) and the first cold contact point 35B (the inner surface of the sheath 16) is utilized to generate an electromotive force (voltage) by a Seebeck effect. The voltage generated at the first thermoelectric converter 35 is accumulated in the tank 38 after being converted into a suitable voltage at the electric power converter 41. An endothermic action caused by driving the first thermoelectric converter 35 removes the heat remaining in the first gripping piece 25 (vibration transmitting portion 14), and rapidly cools the first gripping piece 25 to around room temperature.

At the second thermoelectric converter 36, the temperature difference between the second hot contact point 36A (the second gripping piece 26) and the second cold contact point 36B (the inner surface of the cover 26B) is utilized to generate an electromotive force (voltage) by a Seebeck effect. The voltage generated at the second thermoelectric converter 36 is accumulated in the tank 38 after being converted into a suitable voltage at the electric power converter 41. An endothermic action caused by driving the second thermoelectric converter 36 removes the heat remaining in the second gripping piece 26, and rapidly cools the second gripping piece 26 to around room temperature.

Furthermore, at the third thermoelectric converter 37, the temperature difference between the third hot contact point 37A (the heater 27) and the third cold contact point 37B (the inner surface of the sheath 16) is utilized to generate an electromotive force (voltage) by a Seebeck effect. The voltage generated at the third thermoelectric converter 37 is accumulated in the tank 38 after being converted into a suitable voltage at the electric power converter 41. An endothermic action caused by driving the third thermoelectric converter 37 removes the heat remaining in the heater 27 and the second gripping piece main body 26A on which the heater 27 is provided, and rapidly cools the heater 27 (the second gripping piece 26) down to around room temperature.

In the above manner, the first gripping piece 25, the second gripping piece 26, and the heater 27 are rapidly cooled by the action of the first to third thermoelectric converters 35 to 37, which allows the operator to use the energy treatment device 11 to not only perform treatment on the treatment target, but also to perform treatment as an ordinary forceps. In other words, this allows the open motion of the second gripping piece 26 to be utilized for stretching spaces between the biotissues, and allows the first gripping piece 25 and the second gripping piece 26 to be utilized for clutching the biotissue.

Upon releasing the depressed operation button 45, the control circuit 34 controls the second switch portion 43 so that the battery unit 13 (the tank 38) and the first to third amplifier circuits 31 to 33 become a disconnected state, in which they are electrically disconnected, from the above connected state. In the same manner as in the case of the first switch portion 42, the second switch portion 43 may be switched from the connected state to the disconnected state immediately after releasing the depressed operation button 45, or after a predetermined time (several seconds to several tens of seconds) from releasing the depressed operation button 45. The control circuit 34 controls the charge circuit 44 to charge the battery unit 13 by utilizing the electric energy accumulated in the tank 38. In the case where the remaining amount of electric energy accumulated at the tank 38 becomes zero or close to zero, the charge circuit 44 ends charging of the battery unit 13.

In the case where the operator depresses the operation button 45 again to restart using the energy treatment device 11, the control circuit 34 controls the first switch portion 42 so that the first to third thermoelectric converters 35 to 37 and the tank 38 become a disconnected state, in which they are electrically disconnected, from the above connected state. The control circuit 34 controls the second switch portion 43 so that the battery unit 13 and the first to third amplifier circuits 31 to 33 become a connected state in which they are electrically connected, from the above disconnected state. In this manner, the electric power is supplied from the battery unit 13 to the first to third amplifier circuits 31 to 33, to allow various kinds of energies to be output from the treatment portion 24. In the case where the electric energy remains in the tank 38, the electric energy can be supplied to the first to third amplifier circuits 31 to 33, and output from the treatment portion 24 as various kinds of energies.

According to the first embodiment, the energy treatment device 11 comprises the treatment portion 24 that receives a supply of energy and treats a treatment target, the controller that controls the supply of energy with respect to the treatment portion 24, the converter that is configured to transmit heat energy generated along with the treatment of the treatment target, and converts a temperature difference into an electric energy, and the receiver that receives the electric energy converted at the converter.

According to this configuration, the receiver is able to receive the electric energy generated at the converter. The energy of the receiver can then be passed on to the treatment portion 24 again, allowing effective utilization of the heat energy. Furthermore, by operating the converter, it is possible to prompt cooling of the treatment portion 24, allowing the treatment portion 24 to be used for purposes other than the energy treatment after it is returned to room temperature. If the cooling of the treatment portion 24 can be prompted, in the case where the treatment portion 24 comes in contact with surrounding tissues other than the treatment target, the risk of applying damage to the surrounding tissues can be reduced.

The converter converts the heat energy into the electric energy by the temperature difference between the treatment portion 24 that is heated by the applied energy and a portion that has a lower temperature than the treatment portion 24. According to this configuration, power can be generated at the converter by utilizing the heat energy of the treatment portion 24 that has risen to a high temperature by the supply of energy. This allows power to be generated efficiently. The treatment portion 24 may also be rapidly cooled by utilizing the converter. Therefore, even in the case where the treatment portion 24 unintentionally comes in contact with the surrounding tissues, the risk of damaging the surrounding tissues can be reduced.

The energy treatment device 11 comprises a switch portion that electrically disconnects the converter and the receiver when the energy is supplied to the treatment portion 24, and electrically connects the converter and the receiver when the supply of energy to the treatment portion 24 is stopped.

According to this configuration, during the so-called used state, the converter and the receiver can be electrically disconnected. This, for example, prevents the occurrence of a state in which the converter is operated and absorbs heat of the treatment portion 24 while treatment is being performed. Furthermore, in the so-called unused state, the converter and the receiver can be electrically connected, and the treatment portion 24 can be rapidly cooled. Therefore, even in the case where the treatment portion 24 unintentionally comes in contact with the surrounding tissues, the risk of applying damage to the surrounding tissues can be reduced.

The receiver comprises a battery that can be charged with the electric energy generated at the converter, and a charge circuit 44 that charges the electric energy to the battery. According to this configuration, the electric energy generated at the converter can be accumulated in the battery, and can be fetched and made use of when necessary. Therefore, the heat energy can be effectively utilized at the energy treatment device 11, and power-saving of the energy treatment device 11 can be promoted.

The receiver comprises the tank 38 which temporary accumulates the electric energy converted at the converter. The charge circuit 44 performs battery charging from the tank 38 when the treatment portion 24 is not performing treatment. Generally, there is a stronger tendency for the tank 38 that temporary accumulates electric energy to lose electric energy by electric discharge in comparison to the battery that accumulates the electric energy by using chemical change. According to this configuration, under a circumstance where the electric energy is not used immediately, the electric energy in the tank 38 can be charged to the battery side and maintained in the battery for a comparatively long period. This prevents the loss of electric energy in the tank 38, and realizes power-saving of the energy treatment device 11.

The treatment portion 24 comprises a pair of clamping members, at least one of which is rotatable with respect to the other. According to this configuration, the treatment portion 24 is rapidly cooled to a low temperature by the endothermic action of the converter. After cooling, the pair of clamping members is used as normal forceps. In the above manner, the operator is able to reduce frequently replacing the energy treatment device 11 with the forceps during surgery, which would improve the operator's convenience, and shorten the time of surgery.

In the present embodiment, the receiver that receives the electric energy converted at the first to third thermoelectric converters 35 to 37 (converter) is configured by the tank 38 and the battery; however, the receiver is not limited to this example. The receiver may also be configured merely by a resistor (an electric wire) to apply the electric currents of the first to third thermoelectric converters 35 to 37 to the resistor. In this case, the electric currents generated at the first to third thermoelectric converters 35 to 37 would not be accumulated. Furthermore, in this case, the endothermic action of the first to third thermoelectric converters 35 to 37 would be used mainly for the purpose of cooling the treatment portion 24.

[Second Embodiment]

Figure 5:
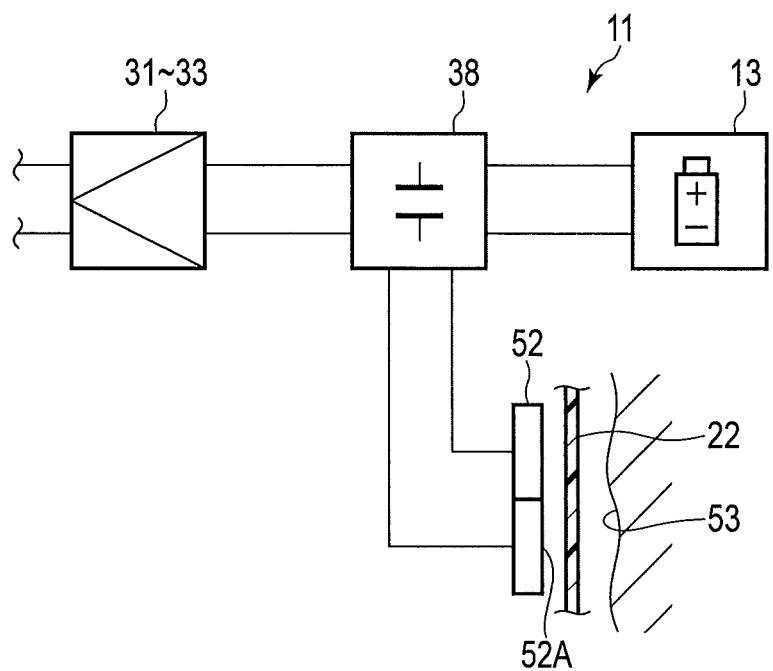
FIG. 5 is a block diagram showing configurations of a fourth thermoelectric converter, a battery unit, and a tank of an energy treatment device of a second embodiment.

With reference to FIG. 5, a second embodiment of an energy treatment device 11 will be explained. The energy treatment device 11 of the second embodiment differs from that of the first embodiment in that a fourth thermoelectric converter 52 that generates power by the body temperature of an operator is provided instead of the first to third thermoelectric converters 35 to 37. The other parts are identical to the first embodiment. Therefore, mainly the parts different from those of the first embodiment will be explained, and illustrations or explanations of the parts identical to those of the first embodiment will be omitted.

The fourth thermoelectric converter 52 is provided, for example, inside a housing 12 (on an inner surface of the housing 12). The fourth thermoelectric converter 52 is configured by a so-called thermocouple, and comprises a fourth hot contact point 52A and a fourth cold contact point. The fourth hot contact point 52A is fixed on the inner surface of a grip 22 of the housing 12. The fourth cold contact point is fixed to a metal part inside the housing 12, such as a frame for securing rigidity, or a heat discharge plate provided on a housing main body 21 side.

A first switch portion 42 and a second switch portion 43 are configured by a general relay circuit. Under the control of a control circuit 34, the first switch portion 42 is capable of switching between a connected state in which the fourth thermoelectric converter 52 and a tank 38 are electrically connected, and a disconnected state in which the fourth thermoelectric converter 52 and the tank 38 are electrically disconnected.

In the following, with reference to FIG. 5, an operation of the energy treatment device 11 of the present embodiment will be explained. In a state where the housing 12 is gripped by the operator, when the operator clutches the treatment target with the treatment portion 24 by operating a handle 18 and operates an operation button 45A in such state, an energy in a mode suitable for incising the treatment target (biotissue) is provided to the treatment portion 24. When an operation button 45B is operated, an energy in a mode suitable for coagulating the treatment target (biotissue) is provided to the treatment portion 24.

An electric power supplied from a battery unit 13 is supplied to first to third amplifier circuits 31 to 33 via a second switch portion 43 under the control of the control circuit 34, is converted into a suitable electric energy at each of the first to third amplifier circuits 31 to 33, and is output from the treatment portion 24 as an ultrasonic energy, a high-frequency energy, and a heat energy. In the case where the electric energy is accumulated in the tank 38, the electric energy may be supplied to the first to third amplifier circuits 31 to 33, and converted into a suitable electric energy at each of the first to third amplifier circuits 31 to 33, so that various kinds of energies are output from the treatment portion 24. In the used state where various kinds of energies are output from the treatment portion 24, the second switch portion 43 is in a connected state in which the battery unit 13 and the first to third amplifier circuits 31 to 33 are electrically connected. However, in the used state, the first switch portion 42 is in a disconnected state, in which the fourth thermoelectric converter 52 and the tank 38 are electrically disconnected.

In the case where the operator has completed or suspended the treatment, and has released the depressed operation button 45 to become an unused state, the control circuit 34 controls the first switch portion 42 to bring the fourth thermoelectric converter 52 and the tank 38 to a connected state where they are electrically connected, from the above disconnected state.

In this state, at the fourth thermoelectric converter 52, a temperature difference between the fourth hot contact point 52A (the grip 22 warmed by an operator's hand 53) and the fourth cold contact point 52B (the frame or the heat discharge plate) is utilized to generate an electromotive force (voltage) by a Seebeck effect. The voltage generated at the fourth thermoelectric converter 52 is converted into a suitable voltage at the electric power converter 41, and accumulated in the tank 38.

Upon releasing the depressed operation button 45, the control circuit 34 controls the second switch portion 43 so that the battery unit 13 (the tank 38) and the first to third amplifier circuits 31 to 33 become a disconnected state in which they are electrically disconnected from the above connected state. The control circuit 34 controls the charge circuit 44 to charge the battery unit 13 by utilizing the electric energy accumulated in the tank 38.

In the case where the operator depresses the operation button 45 again to restart using the energy treatment device 11, the control circuit 34 controls the first switch portion 42 so that the fourth thermoelectric converter 52 and the tank 38 become a disconnected state, in which they are electrically disconnected from the above connected state. The control circuit 34 controls the second switch portion 43 so that the battery unit 13 and the first to third amplifier circuits 31 to 33 become a connected state, in which they are electrically connected from the above disconnected state. In this manner, the electric power is supplied from the battery unit 13 to the first to third amplifier circuits 31 to 33, to allow various kinds of energies to be output from the treatment portion 24. In the case where the electric energy remains in the tank 38, the electric energy can be supplied to the first to third amplifier circuits 31 to 33, and output from the treatment portion 24 as various kinds of energies.

According to the present embodiment, a body temperature of an operator can be utilized to generate power. The generated electric power can be used for treatment to realize a power-saving energy treatment device 11.

The present invention is not limited to the above-described embodiments, and can be modified as appropriate in practice without departing from the gist of the invention. In other words, in each of the above embodiments, the tank 38 is provided in the housing 12 (hand piece). However, the tank 38 may also be provided on the power source device (power source box) side which is separated from the housing 12. In this case, the housing 12 and the power source device (tank 38) are electrically connected via a cable in which an electric wire is accommodated. In addition, it is, of course, possible to combine the energy treatment devices 11 of each of the above embodiments to configure one energy treatment device 11.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment device comprising:
   a treatment portion configured to receive a supply of energy to treat a treatment target;
   a controller configured to control the supply of energy with respect to the treatment portion;
   a converter configured to receive heat energy generated during treatment of the treatment target, and the converter is configured to convert the received heat energy into electric energy based on a temperature difference between (i) heat generated by energy applied by the treatment portion, and (ii) a portion of the energy treatment device that has a lower temperature than the treatment portion;
   a receiver configured to receive the electric energy converted by the converter; and
   a switch configured to electrically disconnect the converter and the receiver when the energy is supplied to the treatment portion, and the switch is configured to electrically connect the converter and the receiver when the supply of energy to the treatment portion is stopped.

2. The energy treatment device according to claim 1, wherein the receiver includes:
   a battery configured to be charged with the electric energy generated by the converter, and
   a charge circuit configured to charge the battery with the electric energy.

3. The energy treatment device according to claim 2, wherein:
   the receiver includes a tank that temporary accumulates the electric energy converted at the converter, and
   the charge circuit performs battery charging from the tank to the battery when the treatment portion is not performing treatment.

4. The energy treatment device according to claim 1, wherein the treatment portion includes a pair of clamping members, and at least one clamping member of the pair of clamping members is rotatable with respect to another clamping member of the pair of clamping members.

* * * * *